US005681698A

United States Patent [19]
Hogan et al.

[11] Patent Number: 5,681,698
[45] Date of Patent: Oct. 28, 1997

[54] 23S RRNA NUCLEIC ACID PROBES TO *MYCOBACTERIUM KANSASII*

[75] Inventors: James J. Hogan; Philip W. Hammond, both of San Diego, Calif.

[73] Assignee: Gen-Probe Incorporated, San Diego, Calif.

[21] Appl. No.: 180,762

[22] Filed: Jan. 5, 1994

Related U.S. Application Data

[63] Continuation of Ser. No. 691,314, Apr. 25, 1991, abandoned.

[51] Int. Cl.$^6$ .............................. C12Q 1/68; C12P 19/34; C07H 21/04
[52] U.S. Cl. .................... 435/6; 435/91.2; 536/24.32; 536/24.33; 935/78
[58] Field of Search ...................... 435/6, 91.2; 935/78; 536/23.7, 24.32, 24.33

[56] References Cited

U.S. PATENT DOCUMENTS 5,030,557  7/1991  Hogan et al. ............................... 435/6

OTHER PUBLICATIONS

Taber et al., U.S. Patent 4,689,295, Jun. 17, 1984.
Webster WO 8301073, 1983.
Gen-Probe Partners, WO 84/02721, 1984.
Webster, EPA 0155359, 1985.
Hogan et al., PCT WO88/03957, 1988.
Carrico et al., AU-A-31387/84, 1985.
Lane et al., 82 Proc. Natl. Acad. Sci. USA p. 6955, (1985).
Rogers et al., 82 Proc. Natl. Acad. Sci. USA p.1160, (1985).
Brosius et al., 75 Proc. Natl. Acad. Sci., USA p. 4801, (1978).
Brosius et al., 77 Proc. Natl. Acad. Sci., USA p. 201, (1980).
Weisburg et al., 167 Journal of Bacteriology p. 570, (1986).
Kohne, American Clinical Products Review, Nov. 1986.
Brenner, in Impact of Biotechnology on Microbial Detection, Estimation, and Characterization, B. Swaminathan et al., eds. Dekker, Inc., New York, p. 42 (1986).
Razin, 49 Microbiological Review p. 419, (1985).
Crosa et al., 83 Journal of General Microbiology 271, (1974).
Clinical Microbiology Newsletter 90, (1987).
Stahl, 4 Biotechnology p. 623, (1986).
Brenner et al., 90 Annals of Internal Medicine p. 656, (1979).
Ludwig and Stackebrandt, 135 Archives of Microbiology p. 45, (1983).
Brenner et al., 1 Current Microbiology p. 71, (1978).
Kohne et al., In Thornsbury et al., *Legionella* Proceedings of the Second International Symposium, American Society for Microbiology, Washington, 107 (1984).
Benner et al. of Systematic Bacteriol, vol. 1 Bergey's Manual, p. 238, 1984.
Brenner et al., 35 International Journal of Systematic Bacteriology p. 50, (1985).
Grimont et al., vol. 21 J. Clin. Microbiol. p. 431, (1985).
Brenner et al., vol. 30 International Journal SB p. 236, (1980).
Brenner, vol. 1 Bergy's Manual of Systematic Bacteriology p. 160, (1984).
Festl et al., vol. 52 Applied and Environmental Microbiology p. 1190, (1986).
Carbon et al., vol. 9 Nucleic Acid Research p. 2325, (1981).
Colwell et al., vol. 24 International Journal of Systematic Bacteriology p. 422, (1974).
Brenner, vol. 23 International Journal of Systematic Bacteriology, p. 298, (1973).
Brenner, vol. 1 Bergy's Manual of Systematic Bacteriology p. 408, (1984).
Veldman et al., v. 9 Nucleic Acids Research p. 6935, (1981).
Kilpper-Balz et al., v. 7 Current Microbiology p. 245, (1982).
Kilpper-Balz and Schleifer, v. 10 FEMS Microbiology Letters p. 357, (1981).
Schleifer and Kilpper-Balz, v. 34 International Journal of Systematic Bacteriology p. 31, (1984).
Harvey and Greenwood, v. 33 International Journal of Systematic Bacteriology p. 275, (1983).
Lau et al., v. 447 System Appl. Microbiol. (1987) p. 432.
Baess v. 91 Adv. Path. Microbiol. Immunol. Scand. Sect. B, p. 201, (1983).
Imaeda, International Journal of Systematic Bacteriology p. 147, (1985).
Baess and Bentzon, vol. 86 Acta Pat. Microbiol. Scand. Sect. B p. 71, (1978).
Drake at al., vol. 25 Journal Clinical Microbiology, (1987), p. 252.
Stackebrandt and Schleifer, in Biological Biochemical, Biochemical Aspects of Actinomycetes p. 485, (1984).
Goodfellow and Minnikin, In The Mycobacteria, Kubica and Wayne, eds. Dekker, (1984) p. 167.
Mordarski et al., vol. 118 Journal of General Microbiology p. 313, (1980).
Goodfellow and Wayne, in vol. 1 The Biology of the *Mycobacteria* p. 476, (1982).
Baess, vol. 90 Acta Path. Microbiol. Immunol. Scand. Sect. B. p. 371, (1982).
Bradley, vol. 113, Journal of Bacteriology p. 645, (1973).
Rogers et al., vol. 82 Proc. Natl. Acad. Sci. USA p. 1160, (1985).
Yogev and Razin, vol. 36 International Journal of Systematic Bacteriology p. 426, (1986).

(List continued on next page.)

*Primary Examiner*—Lisa B. Arthur
*Attorney, Agent, or Firm*—Lyon & Lyon LLP

[57] ABSTRACT

This invention discloses hybridization assay probes for *Mycobacterium kansasii* comprised of an oligonucleotide of about 18 nucleotides. These probes hybridize to a variable region of the 23S rRNA gene of *Mycobacterium kansasii*. The oligonucleotide probes are complementary to the rRNA variable region of the rRNA gene. Such probe specificity offers a rapid, non-subjective method of identification and quantitation of a bacterial colony for the presence of selected rRNA sequences capable of distinguishing all strains of *Mycobacterium kansasii*.

22 Claims, No Drawings

OTHER PUBLICATIONS

Razin et al., vol. 135 Ann. Microbiol. p. 9, (1984).

Gobel et al., vol. 133 Journal of General Microbiology p. 1969, (1987).

Gobel vol. 226 Science p. 1211, (1984).

Razin, vol. 49 Microbiol. Rev. p. 437, 1985.

Jones and Collins, Bergy's Manual of Systematic Bacteriology p. 1261, 1986.

Boddinghaus et al., 28 J. Clin. Micro. p. 1751, 1990 abstract.

Rogall et al., vol. 40 Int. J. Sys. Bact. p. 323, 1990, abstract.

Rogall et al., vol. 136 J. Gen. Micro. p. 1915, 1990 abstract.

Stahl and Urbance vol. 172 J. Bact. pp. 116–124 1990 abstract.

Killian vol. 93 J. Gen. Micro. p. 9, 1976 (abstract).

Musser et al., vol. 52 Inf. Imm. 183, p. 1986 (abstract).

Malouin et al., vol. 26 J. Clin. Micro. p. 2132, 1988.

Carrico, et al., EPA 0133671, Mar. 6, 1985.

Gobel et al., EP 0250662 Jan. 7, 1988.

Uchida et al., EP 0277237, Aug. 10, 1986.

Marliere et al., EP 0245129, Nov. 11, 1987.

Rashtchian, EP 0232085, Aug. 12, 1987.

Earnshaw, W.C. et al. (1987) Journal of Cell Biology, vol. 104, "Molecular Cloning of cDNA for CENP–B, the major human centromere autoartigen", pp. 817–829.

Krumholz, L. R. et al. (1989) "Nucleotide Sequence of the *UNC* operon of *Vibrio alginolyticus*", Nucleic Acids Research 17 (19):7993–7994.

Regensburger A. et al. (1988) Journal of General Microbiology 134:1197–1204, "DNA Probes with Different Specificities from a Cloned 23S rRNA Gene of *Micrococcus luteus*".

Liesack et al. (1990) Letters in Applied Microbiology, vol. 11, "Development of a highly specific diagnostic 23S rDNA oligonucleotide probe for *Myaobacterium leprae*", pp. 96–99.

Betzl, D. et al. (Se. 1990) Applied and Environmental Microbiology, vol. 56(9), "Identification of Lactococci and Enterococci by Colony Hybridization with 23S rRNA–targeted Oligonucleotide Probes", pp. 2927–2929.

Arnold, L. et al. (1989) Clinical Chemistry, vol. 35/8," Assay Format Involving Acridinium–Ester–Labeling DNA Probes", pp. 1588–1594.

Stahl, D. A. et al. (Jan. 1990) Journal of Bacteriology, "The Division between Fast–and Slow–Growing Species Corresponding to Natural Relationships amoung the Mycobacteria", vol. 172(1), pp. 116–124.

R. B. Wallace and C. G. Miyada Methods in Enzymology 152, 432–442 (1987).

ATCC Catalogue of Bacteria and Bacteriophages (17th ed.), pp. 136–144 (1989).

U. Edwards, T. Rogall, H. Blöcker, M. Emde and E. C. Böttger Nucleic Acids Research 17, 7843–7853 (1989).

23S RRNA NUCLEIC ACID PROBES TO *MYCOBACTERIUM KANSASII*

This application is a continuation of application Ser. No. 07/691,314, filed Apr. 25, 1991 now abandoned.

FIELD OF THE INVENTION

The inventions described and claimed herein relate to the design and construction of nucleic acid probes to *Mycobacterium kansasii* which are capable of detecting said organism in test samples of, e.g., sputum, urine, blood and tissue sections, food, soil and water.

INCORPORATION BY REFERENCE OF RELATED PATENTS & APPLICATIONS

The following applications are incorporated by reference in their entirety together with all other applications cited herein:

1) U.S. Pat. No. 4,851,330 to Kohne, entitled "Method For Detection, Identification and Quantitation of Non-Viral Organisms" issued Jul. 25, 1989;

2) PCT Patent Application No. PCT/US87/03009 to Hogan et. al., entitled "Nucleic Acid Probes for Detection and/or Quantitation of Non-Viral Organisms," International Publication Number WO 88/03957, published Jun. 2, 1988.

3) U.S. application Ser. No. 816,711 entitled "Accelerated Nucleic Acid Reassociation Method," filed Jan. 7, 1986, abandoned in favor of U.S. application Ser. No. 644,879 filed Jan. 23 1991; issued as U.S. Pat. No. 5,132,207 allowed Feb. 7, 1992, assigned to Gen-Probe Incorporated, Apr. 14, 1986, Reel/Frame 4538/0494, also published under European Patent Application Publication Number 0 299 422, Jul. 22, 1987 and 4) U.S. application Ser. No. 841,860 entitled "Method for Releasing RNA and DNA from Cells," filed Mar. 20, 1986, abandoned doned in favor of U.S. application Ser. No. 298,765 filed Jan. 17, 1989 which was issued as U.S. Pat. No. 5,374,522 abandoned in favor of U.S. Ser. No. 711,114, filed Jun. 21, 1991, assigned to Gen-Probe Incorporated, May 23, 1986, Reel/Frame 4566/0901, also published under European Patent Application Publication Number 0 288 618, Feb. 11, 1988.

5) U.S. application Ser. No. 613,603 entitled "Homogeneous Protection Assay" filed Nov. 8, 1990, which issued as U.S. Pat. No. 5,283,174, assigned to Gen-Probe Incoporated Mar. 6, 1992, Reel/Frame 6057/0433-34, also published under European Patent Application Publication Number 0 309 230, Mar. 29, 1989.

6) EPO Application No. PCT/US88/03361 entitled "Acridinium Ester Labeling and Purification of Nucleotide Probes" filed Oct. 5, 1988.

7) U.S. Pat. No. 5,030,557 entitled "Means and Methods for Enhancing Nucleic Acid Hybridization," allowed Dec. 17, 1990, filed Nov. 24, 1987.

BACKGROUND

Two single strands of deoxyribo- ("DNA") or ribo-("RNA") nucleic acid, comprised of nucleotides (adenosine 5' phosphoric acid, cytidine 5'-phosphoric acid, deoxythymidine 5'-phosphoric acid, guanosine 5'-phosphoric acid, uridine 5'-phosphoric acid, inosine 5'-phosphoric acid, etc.) may associate ("hybridize") to form a double helical structure in which the two polynucleotide chains running in opposite directions are held together by hydrogen bonds (a weak form of chemical bond) between pairs of matched, centrally located compounds known as "bases." Generally, in the double helical structure of nucleic acids, the base adenine (A) is hydrogen bonded to the base thymine (T) or uracil (U) while the base guanine (G) is hydrogen bonded to the base cytosine (C). At any point along the chain, therefore, one may find the classical "Watson-Crick" base pairs AT or AU, TA or UA, GC, or CG. One may also find AG, GU and other "wobble" or mismatched base pairs in addition to the traditional ("canonical") base pairs. Assuming that a first single strand of nucleic acid is sufficiently complementary to a second and that the two are brought together under conditions which will promote their hybridization, double stranded nucleic acid will result. Under appropriate conditions, DNA/DNA, RNA/DNA, or RNA/RNA hybrids may be formed.

A probe may be a single strand nucleic acid sequence which is complementary in some particular degree to the nucleic acid sequences sought to be detected ("target sequences"). It may also be labelled with a detectable moiety such as a radioisotope, antigen or chemiluminescent moiety. A background description of the use of nucleic acid hybridization as a procedure for the detection of particular nucleic acid sequences is described in U.S. Pat. No. 4,851,330 to Kohne and entitled "Method for Detection, Identification and Quantitation of Non-Viral Organisms," issued Jul. 25, 1989 and in EPO Patent Application No. PCT/US87/03009 to Hogan et al., entitled "Nucleic Acid Probes for Detection and/or Quantitation of Non-Viral Organisms."

Also described in the Kohne patent and the Hogan et al. application are methods for determining the presence of RNA-containing organisms in a sample which might contain such organisms. These methods require the mixture of nucleic acids from a sample and a probe comprised of nucleic acid molecules which are shorter than the ribosomal-RNA ("rRNA") subunit sequence from which it was derived. The probes are sufficiently complementary to hybridize to the rRNA of one or more non-viral organisms or groups of non-viral organisms. The mixture is then incubated under specified hybridization conditions, and assayed for hybridization of the probe and any test sample rRNA.

Further, the Hogan et al. application describes numerous probes which detect only specifically targeted rRNA subunit subsequences in particular organisms or groups of organisms in a sample, even in the presence of many non-related organisms, or in the presence of closest known phylogenetic neighbors. The Hogan et al. application discloses hybridization assay probes for *Mycobacterium avium, Mycobacterium intracellulare, Mycobacterium tuberculosis, Mycobacterium africanum, Mycobacterium bovis, Mycobacterium microti*, the genus Mycobacterium, *Mycoplasma pneumoniae*, the genus Legionella, *Chlamydia trachomatis*, the genus Campylobacter, Enteroccoccus, the genus Pseudomonas group I, *Enterobacter cloacae, Proteus mirabilis*, the genus Salmonella, *Escherichia coli*, bacteria, fungi, and *Neisseria gonorrhoeae*. Such probe sequences do not cross react with nucleic acids from the groups listed above or any other bacterial species or infectious agent, under proper stringency.

This invention discloses and claims novel probes for the detection of *Mycobacterium kansasii*. These probes are capable of distinguishing between *Mycobacterium kansasii* and its known closest phylogenetic neighbors.

SUMMARY OF THE INVENTION

We have discovered and describe herein novel probes to *Mycobacterium kansasii*. These probes which detect unique rRNA and rRNA gene sequences may be used in an assay for the detection and/or quantitation of *Mycobacterium kansasii*.

Particularly, this invention discloses hybridization assay probes for *Mycobacterium kansasii*comprised of an oligonucleotide of about 18 nucleotides. These probes hybridize to a variable region of the 23 S rRNA gene unique to *Mycobacterium kansasii.* The oligonucleotide probes are substantially complementary to the rRNA variable region of the rRNA gene. Such probe specificity offers a rapid, non-subjective method of identification and quantitation of a bacterial colony for the presence of specific rRNA sequences unique to all strains of *Mycobacterium kansasii.*

DEFINITIONS

The following terms, as used in this disclosure and claims, are defined as:

nucleotide: a subunit of a nucleic acid consisting of a phosphate group, a 5-carbon sugar and a nitrogen containing base. In RNA the 5-carbon sugar is ribose. In DNA, it is a 2-deoxyribose. For a 5-nucleotide, the sugar contains a hydroxyl group (—OH)at the carbon-5. The term also includes analogs of such subunits.

nucleotide polymer: at least two nucleotides linked by phosphodiester bonds. Such nucleotides could be contiguous or non-contiguous.

non-nucleotide unit: unit which does not significantly participate in hybridization of a polymer. Such units must not, for example, participate in any significant hydrogen bonding with a nucleotide, and would exclude units having as a component one of the five nucleotide bases or analogs thereof.

oligonucleotide: a nucleotide polymer generally about 10 to about 100 nucleotides in length, but which may be greater than 100 or shorter than 10 nucleotides in length.

nucleic acid probe: a single stranded nucleic acid sequence that will combine with a complementary single stranded target nucleic acid sequence to form a double-stranded molecule (hybrid). A nucleic acid probe may be an oligonucleotide or a nucleotide polymer. As a probe it will usually contain a detectable moiety which may be attached to the end(s) of the probe or may be internal to the sequence of the probe. The nucleotides which combine with the target nucleic acid need not be strictly contiguous as may be the case with a detectable moiety internal to the sequence of the probe.

detectable moiety: A molecule attached to, or synthesized as part of, a nucleic acid probe. This molecule should be uniquely detectable and will allow the probe to be detected as a result. These detectable moieties are often radioisotopes, chemiluminescent molecules, enzymes, haptens, or even unique oligonucleotide sequences.

hybrid: the complex formed between two single stranded nucleic acid sequences by Watson-Crick base pairings or non-canonical base pairings between the complementary bases.

hybridization: the process by which two complementary strands of nucleic acids combine to form double stranded molecules ("hybrids").

complementarity:a property conferred by the base sequence of a single strand of DNA or RNA which may form a hybrid or double stranded DNA:DNA, RNA:RNA or DNA:RNA through hydrogen bonding between Watson-Crick base pairs on the respective strands. Adenine (A) usually complements thymine (T) or uracil (U), while guanine (G) usually complements cytosine (C).

mismatch: Any pairing, in a hybrid, of two nucleotides which do not form canonical Watson-Crick hydrogen bonds. In addition, for the purposes of the following discussions, a mis-match can include an insertion or deletion in one strand of the hybrid, relative to the other, which results in an unpaired nucleotide(s).

stringency: term used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid.

probe specificity: characteristic of a probe which describes its ability to distinguish between target and non-target sequences. Probe specificity is dependent on sequence and assay conditions and may be absolute (i.e., probe able to distinguish between target organisms and any nontarget organisms), or it may be functional (i.e., probe able to distinguish between the target organism and any other organism normally present in a particular sample). Many probe sequences can be used for either broad or narrow specificity depending on the conditions of use.

variable region: nucleotide polymer which differs by at least one base between the target organism and non-target organisms contained in a sample.

conserved region: a region which is not variable.

bacteria: members of the phylogenetic group eubacteria, which is considered one of the three primary kingdoms.

sequence divergence: process by which nucleotide polymers become less similar during evolution.

sequence convergence: Process by which nucleotide polymers become more similar during evolution.

Tm: temperature at which 50% of the probe is converted from the hybridized to the unhybridized form.

DESCRIPTION OF THE INVENTION

We have discovered DNA probes complementary to a particular rRNA sequence obtained from *Mycobacterium kansasii.* Furthermore, we have successfully used those probes in a specific assay for the detection of *Mycobacterium kansasii*, distinguishing *M. kansasii*from its known, most closely related taxonomic or phylogenetic neighbors.

With the exception of viruses, all prokaryotic organism contain rRNA genes encoding 5S rRNA, 16 S rRNA and a larger rRNA molecule known as23S rRNA. Using methods known to those skilled in the art, we have identified variable regions of rRNA sequences from the 23 S rRNA of *Mycobacterium kansasii.* This included partially or fully sequencing the rRNA of *Mycobacterium kansasii* and closely related phylogenetic neighbors, aligning the sequences to reveal areas of maximum homology and examining the alignment for regions with sequence variation.

With respect to sequencing, complementary oligonucleotide primers of about 10–100 bases in length can be hybridized to conserved regions in purified rRNA that are specific to the 5S, 16S, or 23S subunits and extended with the enzyme reverse transcriptase. Chemical degradation or dideoxynucleotide-terminated sequencing reactions can be used to determine the nucleotide sequence of the extended product. Lane, D. J. et al., *Proc. Natl Acad. Sci. USA* 82, 6955–6959(1985). In a less preferred method, genomic ribosomal RNA sequences may also be determined.

It is not always necessary to determine the entire nucleic acid sequence in order to obtain a probe sequence. Extension from any single oligonucleotide primer can yield up to 300–400 bases of sequence. When a single primer is used to partially sequence the rRNA of the target organism and organisms closely related to the target, an alignment can be made as outlined below. Plainly, if a useful probe sequence is found, it is not necessary to continue rRNA sequencing using other primers. If, on the other hand, no useful probe sequence is obtained from sequencing with a first primer, or if higher sensitivity is desired, other primers can be used to obtain more sequences. In those cases where patterns of variation for a molecule are not well understood, more sequence data may be required prior to probe design.

After sequencing, the sequences are aligned to maximize homology. The rRNA molecule has a close relationship of secondary structure to function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be "aligned" based on the conserved primary sequence and also on the conserved secondary structure elements. Once sequences are aligned it is possible to find the regions in which the primary sequence is variable.

We have identified variable regions by comparative analysis of rRNA sequences both published in the literature and sequences which we have determined ourselves. Computers and computer programs which may be used or adapted for the purposes here in disclosed are commercially available. Since the sequence evolution at each of the variable regions (for example, spanning a minimum of 10 nucleotides )is, for the most part, divergent, not convergent, we can confidently design probes based on a few rRNA sequences which differ between the target organism and its phylogenetically closest relatives. We have seen sufficient variation between the target organism and the closest phylogenetic relative found in the same sample to design the probe of interest.

We have identified the following useful guidelines for designing probes with desired characteristics. Because the extent and specificity of hybridization reactions such as those described here in are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the probe: target nucleic acid hybrid should be chosen to be compatible with the assay conditions. This may be accomplished by avoiding long A and T rich sequences, by terminating the hybrids with G:C base pairs and by designing the probe with an appropriate Tm. The beginning and end points of the probe should be chosen so that the length and %G and %C result in a Tm about 2°–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as ionic strength of the reaction mixture increases and that the thermal stability of hybrids will increase with increasing ionic strength. On the other hand, chemical reagents, such as formamide, urea, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

Second, probes should be positioned so as to minimize the stability of the probe :nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible. Whether a probe sequence is useful to detect only a specific type of organism depends largely on the thermal stability difference between probe:target hybrids and probe: nontarget hybrids. In designing probes the differences in Tm should be as large as possible.

The length of the target nucleic acid sequence and, accordingly, the length of the probe sequence can also be important In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions of the rRNA which are known to form strong internal structures inhibitory to hybridization are less preferred. Likewise, probes with extensive self-complementarity should be avoided.

As explained above, hybridization is the association of two single strands of complementary nucleic acid to form a hydrogen bonded double strand. It is implicit that if one of the two strands is wholly or partially involved in a hybrid that it will be less able to participate in formation of a new hybrid. In the case of rRNA, the molecule is known to form very stable intramolecular hybrids. By designing a probe so that a substantial portion of the sequence of interest is single stranded the rate and extent of hybridization may be greatly increased. If the target is the genomic sequence corresponding to the rRNA then it will naturally occur in a double stranded form, this is also the case with the product of the polymerase chain reaction (PCR). These double stranded targets are naturally inhibitory to hybridization with a probe. Finally, there can be intramolecular and intermolecular hybrids formed with in a probe if there is sufficient self complementarity. Such structures can be avoided through careful probe design. Computer programs are available to search for this type of interaction.

Once a presumptive unique sequence has been identified, a complementary DNA oligonucleotide is produced. This single stranded oligonucleotide will serve as the probe in the hybridization reaction. Defined oligonucleotides may be produced by any of several well known methods, including automated solid-phase chemical synthesis using cyanoethylphosphoramidite precursors. Barone, A. D. et al., *Nucleic*

Acids Research 12,4051–4060(1984). Other well-known methods for construction of synthetic oligonucleotides may, of course, be employed. 2 J. Sambrook, E. F. Fritsch and T. Maniatis, *Molecular Cloning* 11 (2d ed 1989). The current DNA synthesizers are capable of producing large amounts of nucleic acid.

Once synthesized, selected oligonucleotide probes may also be labelled by any of several well known methods. 2 J. Sambrook, E. F. Fritsch and T. Maniatis, *Molecular Cloning* 11 (2d ed. 1989). Useful labels include radioisotopes as well as non-radioactive reporting groups. Isotopic labels include $^3H$, $^{35}S$, $^{32}P$, $^{125}I$, $^{57}Co$ and $^{14}C$. Most methods of isotopic labelling involve the use of enzymes and include the known methods of nick translation, end labelling, second strand synthesis, and reverse transcription. When using radio-labelled probes, hybridization can be detected by autoradiography, scintillation counting, or gamma counting. The detection method selected will depend upon the hybridization conditions and the particular radioisotope used for labelling.

Non-isotopic materials can also be used for labelling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, chemiluminescent molecules, enzymes, cofactors, enzyme substrates, haptens or other ligands. We currently prefer to use acridinium esters.

Following synthesis and purification of a particular oligonucleotide sequence, several procedures may be utilized to determine the acceptability of the final product. The first is polyacrylamide gel electrophoresis, which is used to determine size. 2 J. Sambrook, E. F. Fritsch and T. Maniatis, *Molecular Cloning*, 11.51 (2d ed 1989). Such procedures are known in the art. In addition to polyacrylamide gel electrophoresis, High Pressure Liquid Chromatography ("HPLC") procedures also may be used to determine the size and purity of the oligonucleotide product. These procedures are also known to those skilled in the art.

It will be appreciated by those skilled in the art that factors which affect the thermal stability can affect probe specificity and therefore, must be controlled. Thus, the melting profile, including the melting temperature (Tm) of the oligonucleotide/target hybrids should be determined. The preferred method is described in Arnold et al., patent application Ser. No. 613,603 filed Nov. 8, 1990 entitled "Homogeneous Protection Assay which issued as U.S. Pat. No. 5,283,174,".

For Tm measurement using a Hybridization Protection Assay the following technique is used. A probe:target hybrid is formed in target excess in a lithium succinate buffered solution containing lithium lauryl sulfate. Aliquots of this "preformed " hybrid are diluted in the hybridization buffer and incubated for five minutes at various temperatures starting below that of the anticipated Tm (typically 55° C.)and increasing in 2–5 degree increments. This solution is then diluted with a mildly alkaline borate buffer and incubated at a lower temperature (for example 50° C.)for ten minutes. Under these conditions the acridinium ester attached to a single stranded probe is hydrolyzed while that attached to hybridized probe is relatively "protected". This is referred to as the hybridization protection assay ("HPA"). The amount of chemiluminescence remaining is proportional to the amount of hybrid and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In addition to the above method, oligonucleotide/target hybrid melting temperature may also be determined by isotopic methods well known to those skilled in the art. It should be noted that the Tm for a given hybrid will vary depending on the hybridization solution being used because the thermal stability depends upon the concentration of different salts, detergents, and other solutes which affect relative hybrid stability during thermal denaturation. 2 J. Sambrook, E. F. Fritsch and T. Maniatis, *Molecular Cloning*, 9.51 (2d ed 1989).

Rate of hybridization may be measured by determining the $C_0t_{1/2}$. The rate at which a probe hybridizes to its target is a measure of the thermal stability of the target secondary structure in the probe region. The standard measurement of hybridization rate is the $C_0t_{1/2}$ which has units (moles of nucleotide per liter)×(seconds). Expressed more simply it is the concentration of probe times the time at which 50% of maximal hybridization occurs at that concentration. This value is determined by hybridizing various amounts of probe to a constant amount of target for a fixed time. For example, 0.05 pmol of target is incubated with 0.012, 0.025, 0.05, 0.1 and 0.2 pmol of probe for 30 minutes. The amount of hybrid after 30 minutes is measured by HPA as described in the Tm section. The signal is then plotted as a log of the percent of maximum Relative Light Units ("RLU") (from the highest probe concentration) versus probe concentration (moles of nucleotide per liter). RLU are a measurement of the quantity of photons emitted by the labelled-probe measured by the luminometer. The $C_0t_{1/2}$ is found graphically from the concentration corresponding to 50% of maximum hybridization multiplied by the hybridization time in seconds. These values range from $9.0 \times 10^{-6}$ to $9 \times 10^{-5}$ with the preferred values being less than $3.5 \times 10^{-5}$.

The following example sets forth synthetic probes complementary to a unique rRNA sequence, or the corresponding gene, from a target organism, *Mycobacterium kansasii*, and its use in a hybridization assay.

EXAMPLE 1

*Mycobacterium kansasii* is as low-growing photochromogenic bacterium that causes chronic human pulmonary disease resembling tuberculosis (Wayne, L. G. and G. P. Kubica, 1986, The Mycobacteria, pp 1435–1457, In Sneath, P.H.A., N. S. Mair, M. E. Sharpe and J. G. Holt (ed.), Bergey's Manual of Systemic Bacteriology Vol. 2, Williams and Wilkins, Baltimore.). Disseminated infections caused by non-tuberculous mycobacteria such as *M. kansasii* are becoming an increasing public health concern with the expansion of the AIDS epidemic across the United States. *Mycobacterium kansasii* accounted for 3.5% of the pathogenic isolates reported to the Centers for Disease Control in 1980. Classical methods for identification of Mycobacterium rely on staining specimens for acid-fast bacilli followed by culture, colony and cell morphology, growth rate and subsequent biochemical testing. It can take as long as two months to speciate a Mycobacterium isolate using these standard methods.

In particular, differentiation of *M. kansasii* from other closely related organisms, such as *M. avium* and *M. intracellulare*, is difficult be cause of the close relationship at the rRNA level. (Stahl, D. A., Urbance, J. W. 1990, J. Bacteriol. 172:116–124.) Likewise, differentiation of *M. kansasii* and *M. gastri* is especially difficult since some isolates of *M. gastri* resemble *M. kansasii* by Gas liquid chromatogrpahy GLC analysis and the two organisms are closely related at the nucleic acid level. (B. Boddinghaus, T. Rogall, T. Flohr, H. Blocker and E. C. Bottger, 1990 J. Clin. Microbiol. 28:1751–1759, also T. Rogall, T. Flohr and E. C. Bottger, 1990 J. Gen. Microbiol. 136:1915–1920; T. Rogall, J. Wolters, T. Flohr and E. C. Bottger, 1990 Int'l J. System.

Bacteriol. 40:323–330.) The invention herein described offers a rapid, non-subjective and accurate method of identification of M. kansasii and differentiation from the nonpathogenic M gastri and other closely-related organisms as soon as grow this visible.

A probe specific for M kansasii was identified by sequencing with a primer complementary to the 23S rRNA. The following sequence was characterized and shown to be specific for Mycobacterium kansasii, 5'-CGC-TCG-CGC-GCG-ATA-CGC-3'. The phylogenetically near neighbors Mycobacterium gordonae, M. tuberculosis, M. qastri, M. haemophilum were used as comparisons with the sequence of M. kansasii.

This probe is 18 bases in length and hybridizes to the 23S rRNA of M. kansasii corresponding to bases 649–667of E. coli. To demonstrate the reactivity and specificity of the probe for M. kansasii, it was used in a hybridization assay. The probe was first synthesized with a non-nucleotide linker then labelled with a chemiluminescent acridinium ester as described in EPO Patent Application No. PCT/US 88/03361, entitled "Acridinium Ester Labeling and Purification of Nucleotide Probes" filed Oct. 5, 1988. The acridinium ester attached to unhybridized probe is rendered non-chemiluminescent under mild alkaline conditions, while the acridinium ester attached to hybridized probe is relatively resistant. Thus, it is possible to assay for hybridization of acridinium ester-labelled probe by incubation with an alkaline buffer, followed by detection of chemiluminescence in a luminometer. Results are given in Relative Light Units ("RLU"), the quantity of photons emitted by the labelled-probe measured by the luminometer. The conditions of hybridization, hydrolysis and detection are described in Arnold, et al., (Clin. Chem. 35:1588–1594, 1989).

Nucleic acid hybridization was enhanced by the use of "Helper Probes" as disclosed in Hogan et al., U.S. Pat. No. 5,030,557 entitled "Means and Methods for Enhancing Nucleic Acid Hybridization", issued Jul. 9, 1991. Helper probes are oligonucleotides which bind to a portion of the target nucleic acid other than that being targeted by the assay probe, and which imposed new secondary and tertiary structure on the targeted region of the single stranded nucleic acid whereby the rate of binding of the assay probe is accelerated. RNA was hybridized to a mix of the acridinium ester-labeled probes in the presence of un labeled "Helper Probe, " oligonucleotides with the sequence of 5' CGT ATT CAG ACT CGC TTT CGC TGC GGC3'and 5'CCG CTT CGG GTC CAG AAC ACG CCA CTA CAC A 3'. The Tm as determined by the Hybridization Protection Assay disclosed above was 69° C. under these conditions.

In the following experiment, RNA released from one colony or >$10^8$ organisms was assayed. RLU values greater than 30, 000 RLU were considered a positive reaction.

| Target | ATCC# | RLU value |
|---|---|---|
| Mycobacterium avium | 25291 | 3,208 |
| M. bovis | 19210 | 2,739 |
| M. bovis BCG | 35734 | 3,522 |
| M. chelonae | 14472 | 2,576 |
| M. fortuitum | 6841 | 4,019 |
| M. gastri | 15754 | 3,015 |
| M. gordonae | 14470 | 1,885 |
| M. haemophilum | 29548 | 3,165 |
| M. intracellulare | 13950 | 1,373 |
| M. kansasii | 12478 | 123,797 |
| M. kansasii | 25414 | 201,751 |
| M. kansasii | 25101 | 206,062 |
| M. scrofulaceum | 19981 | 2,030 |
| M. simiae | 25275 | 1,764 |
| M. smegmatis | 14468 | 2,378 |
| M. tuberculosis (avir) | 25177 | 3,061 |
| M. tuberculosis (vir) | 27294 | 2,680 |
| M. ulcerans | 19423 | 1,905 |
| M. vaccae | 15483 | 1,905 |
| Nocardia asteroides | 19247 | 3,468 |

The following data show that the probe did not cross react with organisms from a wide phylogenetic cross section.

| Target | ATCC# | RLU value |
|---|---|---|
| Acinetobacter calcoaceticus | 33604 | 5,327 |
| Bacillus subtilis | 6051 | 6,792 |
| Bacteroides fragilis | 23745 | 1,908 |
| Branhamella catarrhalis | 25238 | 2,730 |
| Campylobacter jejune | 33560 | 4,618 |
| Candida albicans | 18804 | 3,188 |
| Chromobacterium violaceum | 29094 | 9,401 |
| Clostridium perfringens | 13124 | 3,684 |
| Deinococcus radiodurans | 35073 | 3,556 |
| Derxia gummosa | 15994 | 2,033 |
| Pseudomonas aeruginosa | 25330 | 4,602 |
| Rahnella aquatilis | 33071 | 2,534 |
| Rhodospirillum rubrum | 11170 | 3,320 |
| Staphylococcus aureus | 12598 | 3,120 |
| Staphylococcus epidermidis | 12228 | 3,106 |
| Streptococcus mitis | 9811 | 2,410 |
| Streptococcus pneumoniae | 6306 | 2,074 |
| Vibrio parahaemolyticus | 17802 | 8,516 |
| Yersinia enterocolitica | 9610 | 4,105 |

The above data confirm that the novel probes herein disclosed and claimed are capable of distinguishing Mycobacterium kansasii from its known nearest phylogenetic neighbors.

We claim:

1. A nucleic acid hybridization assay probe for detecting the presence of *Mycobacterium kansasii* comprising an oligonucleotide 10 to 100 bases in length having at least 10 contiguous bases perfectly complementary to a *Mycobacterium kansasii* nucleic acid variable region, said variable region having at least 10 contiguous bases of a nucleic acid sequence selected from the group consisting of;

5' CGCTCGCGCGCGATACGC (SEQ ID NO: 3), and

5' GCGUAUCGCGCGCGAGCG (SEQ ID NO: 5);

wherein said probe can hybridize to rRNA or rDNA of *Mycobacterium kansasii* under stringent hybridization assay conditions to form a detectable probe:target duplex, but does not hybridize to non-target nucleic acid from *Mycobacterium avium*, *Mycobacterium gordonae*, *Mycobacterium intracellulare*, *Mycobacterium tuberculosis*, *Mycobacterium gastri*, or *Mycobac-*

*terium haemophilum* to form a detectable probe:non-target duplex under said conditions.

2. The nucleic acid probe of claim 1, wherein said probe is 18 to 50 nucleotides in length having a nucleic acid sequence selected from the group consisting of:

5' CGCTCGCGCGCGATACGC (SEQ ID NO: 3),
5' GCGTATCGCGCGCGAGCG (SEQ ID NO: 4),
5' GCGUAUCGCGCGCGAGCG (SEQ ID NO: 5), and
5' CGCUCGCGCGCGAUACGC (SEQ ID NO: 6).

3. A nucleic acid probe for detecting the presence of *Mycobacterium kansasii* comprising an oligonucleotide having at least 10 contiguous bases perfectly complementary to a *Mycobacterium kansasii* nucleic acid variable region, said variable region having at least 10 contiguous bases of a nucleic acid sequence selected from the group consisting of;

5' CGCTCGCGCGCGATACGC (SEQ ID NO:3), and
5' GCGUAUCGCGCGCGAGCG (SEQ ID NO:5);

wherein said probe can hybridize to rRNA or rDNA of *Mycobacterium kansasii* under stringent hybridization assay conditions to form a detectable probe:target duplex, but does not hybridize to non-target nucleic acid from *Mycobacterium avium, Mycobacterium gordonae, Mycobacterium intracellulare, Mycobacterium tuberculosis, Mycobacterium gastri* or *Mycobacterium haemophilum* to form a detectable probe:non-target duplex under said conditions; wherein said probe is about 18 nucleotides in length.

4. The nucleic acid probe of claim 3, wherein said probe consists of a nucleic acid sequence selected from the group consisting of :

5' CGCTCGCGCGCGATACGC (SEQ ID NO: 3),
5' GCGTATCGCGCGCGAGCG (SEQ ID NO: 4),
5' GCGUAUCGCGCGCGAGCG (SEQ ID NO: 5), and
5' CGCUCGCGCGCGAUACGC (SEQ ID NO: 6).

5. The nucleic acid probe of claim 4, wherein said probe is labeled with a detectable moiety.

6. The nucleic acid probe of claim 5, wherein said detectable moiety is selected from the group consisting of: a radioisotope, a chemiluminescent molecule, an enzyme, and a hapten.

7. The nucleic acid probe of claim 6, wherein said detectable moiety is an acridinium ester.

8. A nucleic acid hybrid for facilitating detection of *Mycobacterium kansasii* comprising:

a) a nucleic acid hybridization assay probe able to detect the presence of said *Mycobacterium kansasii* comprising an oligonucleotide 10 to 100 bases in length having at least 10 contiguous bases perfectly complementary to a *Mycobacterium kansasii* nucleic acid variable region, said variable region having at least 10 contiguous bases of a nucleic acid sequence selected from the group consisting of;

5' CGCTCGCGCGCGATACGC (SEQ ID NO: 3), and
5' GCGUAUCGCGCGCGAGCG (SEQ ID NO: 5);

wherein said probe can hybridize to rRNA or rDNA of *Mycobacterium kansasii* under stringent hybridization assay conditions to form a detectable probe:target duplex, but does not hybridize to non-target nucleic acid from *Mycobacterium avium, Mycobacterium gordonae, Mycobacterium intracellulare, Mycobacterium tuberculosis, Mycobacterium gastri*, or *Mycobacterium haemophilum* to form a detectable probe:non-target duplex under said conditions; and b) *Mycobacterium kansasii* nucleic acid having a nucleic acid region corresponding to *nucleotide position 649–667* of *E. coli* 23S rRNA or rDNA.

9. The nucleic acid hybrid of claim 8, wherein said probe is 18 to 50 nucleotides in length having a nucleic acid sequence selected from the group consisting of:

5' CGCTCGCGCGCGATACGC (SEQ ID NO: 3),
5' GCGTATCGCGCGCGAGCG (SEQ ID NO: 4),
5' GCGUAUCGCGCGCGAGCG (SEQ ID NO: 5), and
5' CGCUCGCGCGCGAUACGC (SEQ ID NO: 6).

10. A nucleic acid hybrid for facilitating detection of *Mycobacterium kansasii* comprising:

a) a nucleic acid hybridization assay probe able to detect the presence of said *Mycobacterium kansasii* comprising an oligonucleotide having at least 10 contiguous bases perfectly complementary to a *Mycobacterium kansasii* nucleic acid variable region said variable region having at least 10 continuous bases of a nucleic acid sequence selected from the group consisting of;

5' CGCTCGCGCGCGATACGC (SEQ ID NO: 3), and
5' GCGUAUCGCGCGCGAGCG (SEQ ID NO: 5);

wherein said probe can hybridize to rRNA or rDNA of *Mycobacterium kansasii* under stringent hybridization assay conditions to form a detectable probe:target duplex but does not hybridize to non-target nucleic acid from *Mycobacterium avium, Mycobacterium gordonae, Mycobacterium intracellulare, Mycobacterium tuberculosis, Mycobacterium gastri*, or *Mycobacterium haemophilum* to form a detectable probe:non-target duplex under said conditions; wherein said probe is about 18 nucleotides in length; and b) *Mycobacterium kansasii* nucleic acid having a nucleic acid region corresponding to nucleotide position 649–667 of *E. coli* 23S rRNA or rDNA.

11. The nucleic acid hybrid of claim 10, wherein said probe consists of a nucleic acid sequence selected from the group consisting of:

5' CGCTCGCGCGCGATACGC (SEQ ID NO: 3),
5' GCGTATCGCGCGCGAGCG (SEQ ID NO: 4),
5' GCGUAUCGCGCGCGAGCG (SEQ ID NO: 5), and
5' CGCUCGCGCGCGAUACGC (SEQ ID NO: 6).

12. A probe mix comprising:

a) a nucleic acid hybridization assay probe able to detect the presence of *Mycobacterium kansasii* comprising an oligonucleotide 10 to 100 bases in length having at least 10 contiguous bases perfectly complementary to a *Mycobacterium kansasii* nucleic acid variable region, said variable region having at least 10 contiguous bases of a nucleic acid sequence selected from the group consisting of;

5' CGCTCGCGCGCGATACGC (SEQ ID NO: 3), and
5' GCGUAUCGCGCGCGAGCG (SEQ ID NO: 5);

wherein said probe can hybridize to rRNA or rDNA of *Mycobacterium kansasii* under stringent hybridization assay conditions to form a detectable probe:target duplex, but does not hybridize to non-target nucleic acid from *Mycobacterium avium, Mycobacterium gordonae, Mycobacterium intracellulare, Mycobacterium tuberculosis, Mycobacterium gastri*, or *Mycobacterium haemophilum* to form a detectable probe:non-target duplex under said conditions; and b) a helper probe able to facilitate hybridization of said hybridization probe to *Mycobacterium kansasii* nucleic acid, wherein said helper probe has one or both of the following abilities:

(i) can increase the rate of hybridization of said hybridization probe to said *Mycobacterium kansasii* nucleic acid compared to said rate in the absence of said helper probe, and (ii) can increase the Tm of said probe:target duplex compared to said Tm in the absence of said helper probe.

13. The probe mix of claim 12, wherein said hybridization probe is 18 to 50 nucleotides in length having a nucleic acid sequence selected from the group consisting of:

5' CGCTCGCGCGCGATACGC (SEQ ID NO: 3),
5' GCGTATCGCGCGCGAGCG (SEQ ID NO: 4),
5' GCGUAUCGCGCGCGAGCG (SEQ ID NO: 5), and
5' CGCUCGCGCGCGAUACGC (SEQ ID NO: 6).

14. A probe mix comprising:

a) a nucleic acid hybridization assay probe able to detect the presence of *Mycobacterium kansasii* comprising an oligonucleotide having at least 10 contiguous bases perfectly complementary to a *Mycobacterium kansasii* nucleic acid variable region, said variable region having at least 10 contiguous bases of a nucleic acid sequence selected from the group consisting of:

5' CGCTCGCGCGCGATACGC (SEQ ID NO: 3), and
5' GCGUAUCGCGCGCGAGCG (SEQ ID NO: 5);

wherein said probe can hybridize to rRNA or rDNA of *Mycobacterium kansasii* under stringent hybridization assay conditions to form a detectable probe:target duplex, but does not hybridize to non-target nucleic acid from *Mycobacterium avium, Mycobacterium gordonae, Mycobacterium intracellulare, Mycobacterium tuberculosis, Mycobacterium gastri*, or *Mycobacterium haemophilum* to form a detectable probe:non-target duplex under said conditions; wherein said hybridization probe is about 18 nucleotides in length; and b) a helper probe able to facilitate hybridization of said hybridization probe to *Mycobacterium kansasii* nucleic acid, wherein said helper probe has one or both of the following abilities:

(i) can increase the rate of hybridization of said hybridization probe to said *Mycobacterium kansasii* nucleic acid compared to said rate in the absence of said helper probe, and (ii) can increase the Tm of said probe:target duplex compared to said Tm in the absence of said helper probe.

15. The probe mix of claim 14, wherein said hybridization probe comprises a nucleic acid sequence selected from the group consisting of:

5' CGCTCGCGCGCGATACGC (SEQ ID NO: 3),
5' GCGTATCGCGCGCGAGCG (SEQ ID NO: 4),
5' GCGUAUCGCGCGCGAGCG (SEQ ID NO: 5), and
5' CGCUCGCGCGCGAUACGC (SEQ ID NO: 6).

16. The probe mix of claim 15, wherein said helper probe has a nucleic acid sequence selected from the group consisting of:

CGTATTCAGACTCGCTTTCGCTGCGGC (SEQ ID NO: 1), and
CCGCTTCGGGTCCAGAACACGCCACTACACA (SEQ ID NO: 2).

17. The probe mix of claim 16, wherein said helper probe consists of a nucleic acid sequence selected from the group consisting of:

CGTATTCAGACTCGCTTTCGCTGCGGC (SEQ ID NO: 1), and
CCGCTTCGGGTCCAGAACACGCCACTACACA (SEQ ID NO: 2).

18. A method for determining whether *Mycobacterium kansasii* may be present in a sample comprising the steps of:

a) providing to said sample a nucleic acid hybridization assay probe for detecting the presence of said *Mycobacterium kansasii* comprising an oligonucleotide having at least 10 contiguous bases perfectly complementary to a *Mycobacterium kansasii* nucleic acid variable region, said variable region having at least 10 contiguous bases of a nucleic acid sequence selected from the group consisting of;

5' CGCTCGCGCGCGATACGC (SEQ ID NO: 3), and
5' GCGUAUCGCGCGCGAGCG (SEQ ID NO: 5);

wherein said probe can hybridize to rRNA or rDNA of *Mycobacterium kansasii* under stringent hybridization assay conditions to form a detectable probe:target duplex, but does not hybridize to non-target nucleic acid from *Mycobacterium avium, Mycobacterium gordonae, Mycobacterium intracellulare, Mycobacterium tuberculosis, Mycobacterium gastri*, or *Mycobacterium haemophilum* to form a detectable probe:non-target duplex under said conditions; and b) detecting whether said detectable probe:target duplex is formed as an indication of the presence of *Mycobacterium kansasii*.

19. The method of claim 18, wherein said probe is 18 to 50 bases in length having a nucleic acid sequence selected from the group consisting of:

5' CGCTCGCGCGCGATACGC (SEQ ID NO: 3),
5' GCGTATCGCGCGCGAGCG (SEQ ID NO: 4),
5' GCGUAUCGCGCGCGAGCG (SEQ ID NO: 5), and
5' CGCUCGCGCGCGAUACGC (SEQ ID NO: 6).

20. A method for determining whether *Mycobacterium kansasii* may be present in a sample comprising the steps of:

a) providing to said sample a nucleic acid hybridization assay probe for detecting the presence of said *Mycobacterium kansasii*comprising an oligonucleotide having at least 10 contiguous bases perfectly complementary to a *Mycobacterium kansasii* nucleic acid variable region, said variable region having at least 10 contiguous. bases of a nucleic acid sequence selected from the group consisting of;

5' CGCTCGCGCGCGATACGC (SEQ ID NO: 3), and
5' GCGUAUCGCGCGCGAGCG (SEQ ID NO: 5);

wherein said probe can hybridize to rRNA or rDNA of *Mycobacterium kansasii* under stringent hybridization assay conditions to form a detectable probe:target duplex, but does not hybridize to non-target nucleic acid from *Mycobacterium avium, Mycobacterium gordonae, Mycobacterium intracellulare, Mycobacterium tuberculosis, Mycobacterium gastri*, or *Mycobacterium haemophilum* to form a detectable probe:non-target duplex under said conditions; wherein said probe is about 18 nucleotide in length; and b) detecting whether said detectable probe:target duplex is formed as an indication of the presence of *Mycobacterium kansasii*.

21. The method of claim 20, wherein said probe consists of said nucleic acid sequence.

22. The method 20, wherein said probe consists of a nucleic acid sequence selected from the group consisting of:

5' CGCTCGCGCGCGATACGC (SEQ ID NO: 3),
5' GCGTATCGCGCGCGAGCG (SEQ ID NO: 4),
5' GCGUAUCGCGCGCGAGCG (SEQ ID NO: 5), and
5' CGCUCGCGCGCGAUACGC (SEQ ID NO: 6).

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 1:

CGTATTCAGA CTCGCTTTCG CTGCGGC          27

( 2 ) INFORMATION FOR SEQ ID NO: 2:

( i ) SEQUENCE CHARACTERISTICS:
      ( A ) LENGTH: 31
      ( B ) TYPE: nucleic acid
      ( C ) STRANDEDNESS: single
      ( D ) TOPOLOGY: linear ( i i ) SEQUENCE DESCRIPTION: SEQ ID NO: 2:

CCGCTTCGGG TCCAGAACAC GCCACTACAC A      31

( 2 ) INFORMATION FOR SEQ ID NO: 3:

( i ) SEQUENCE CHARACTERISTICS:
      ( A ) LENGTH: 18
      ( B ) TYPE: nucleic acid
      ( C ) STRANDEDNESS: single
      ( D ) TOPOLOGY: linear ( i i ) SEQUENCE DESCRIPTION: SEQ ID NO: 3:

CGCTCGCGCG CGATACGC      18

( 2 ) INFORMATION FOR SEQ ID NO: 4:

( i ) SEQUENCE CHARACTERISTICS:
      ( A ) LENGTH: 18
      ( B ) TYPE: nucleic acid
      ( C ) STRANDEDNESS: single
      ( D ) TOPOLOGY: linear ( i i ) SEQUENCE DESCRIPTION: SEQ ID NO: 4:

GCGTATCGCG CGCGAGCG      18

( 2 ) INFORMATION FOR SEQ ID NO: 5:

( i ) SEQUENCE CHARACTERISTICS:
      ( A ) LENGTH: 18
      ( B ) TYPE: nucleic acid
      ( C ) STRANDEDNESS: single
      ( D ) TOPOLOGY: linear ( i i ) SEQUENCE DESCRIPTION: SEQ ID NO: 5:

GCGUAUCGCG CGCGAGCG      18

( 2 ) INFORMATION FOR SEQ ID NO: 6:

( i ) SEQUENCE CHARACTERISTICS:
      ( A ) LENGTH: 18
      ( B ) TYPE: nucleic acid
      ( C ) STRANDEDNESS: single
      ( D ) TOPOLOGY: linear ( i i ) SEQUENCE DESCRIPTION: SEQ ID NO: 6:

CGCUCGCGCG CGAUACGC      18